United States Patent [19]
Hawkins et al.

[11] Patent Number: 6,025,138
[45] Date of Patent: Feb. 15, 2000

[54] METHOD FOR DETECTING THE PRESENCE OF A POLYNUCLEOTIDE ENCODING A HYALURONAN RECEPTOR EXPRESSED IN HUMAN UMBILICAL VEIN ENDOTHELIAL CELLS

[75] Inventors: Phillip R. Hawkins, Mountain View; Craig G. Wilde, Sunnyvale; Jeffrey J. Seilhamer, Los Altos Hills, all of Calif.

[73] Assignee: Incyte Pharmaceuticals, Inc., Palo Alto, Calif.

[21] Appl. No.: 08/995,654

[22] Filed: Dec. 22, 1997

Related U.S. Application Data

[62] Division of application No. 08/700,178, Aug. 20, 1996, Pat. No. 5,783,669, which is a division of application No. 08/402,217, Mar. 10, 1995, Pat. No. 5,587,301.

[51] Int. Cl.⁷ .............................. C12Q 1/68; C12N 15/12
[52] U.S. Cl. ........................... 435/6; 536/23.5; 536/24.31
[58] Field of Search .......................... 435/6; 530/388.22; 436/822; 536/23.1, 23.5, 24.3, 24.31

[56] References Cited

FOREIGN PATENT DOCUMENTS

WO93/21312   10/1993   WIPO .

OTHER PUBLICATIONS

Pilarski et al. "Regulated Expression of a Receptor for Hyaluronan–Mediated Motility on Human Thymocytes and T Cells". The Journal of Immunology 150(10):4292–4302, May 1993.

Knudson, C.B and W. Knudson "Hyaluronan–binding proteins in development, tissue homeostasis, and disease", *The FASEB Journal*, 7:1233–1241 (1993).

Orvard, T.C. and J.R.E. Fraser, "Hyaluronan", *The FASEB Journal*, 6:2397–2404 (1992).

Ghosh, P. "The role of hyaluronic acid (hyaluronan) in health and disease: interactions with cells, cartilage and components of synovial fluid" *Clinical and Experimental Rheumatology*, 12: 75–82 (1994).

Akiyama et al., "Introduction: Adhesion molecules in cancer. Part I," *Semin. Cancer Biol.*, 4:215–218 (1993).

Hardwick et al., "Molecular Cloning of a Novel Hyaluronan Receptor That Mediates Tumor Cell Motility," *J. Cell Biol.*, 117:1343–1350 (1992).

Laurent et al., "Hyaluronan," *The FASEB Journal*, 6:2397–2404.

McCourt, P.A.G. et al., "Intercellular Adhesion Molecule–1 Is a Cell Surface Receptor for Hyaluronan", *The Journal of Biological Chemistry*, 269:30081–30084 (1994).

Jaworski, D.M. et al., "BEHAB, a New Member of the Proteoglycan Tandem Repeat Family of Hyaluronan–binding Proteins That is Restricted to the Brain", *The Journal of Cell Biology* 125:495–509 (1994).

Lee, T.H. et al., "A Novel Secretory Tumor Necrosis Factor–inducible Protein (TSG–6) Is a Member of the Family of Hyaluronate Binding Proteins, Closely Related to the Adhesion Receptor CD44" *Journal of Cell Biology*, 116: 545–557 (1992).

*Primary Examiner*—Prema Mertz
*Attorney, Agent, or Firm*—Incyte Pharmaceuticals, Inc.

[57] ABSTRACT

The present invention provides nucleotide and amino acid sequences that identify and encode the hyaluronan receptor (hr) from human umbilical vein endothelial cells. The present invention also provides for antisense molecules to the nucleotide sequences which encode hr, expression vectors for the production of purified HR, antibodies capable of binding specifically to HR, hybridization probes or oligonucleotides for detecting the upregulation of HR encoding nucleotide sequences, genetically engineered host cells for the expression of HR, diagnostic tests for activated, angiogenic, inflamed or metastatic cells and/or tissues based on HR-encoding nucleic acid molecules and antibodies capable of binding specifically to the receptor.

2 Claims, 2 Drawing Sheets

```
  1  MQNLKQKFILEQQEREKLQQKELQIDSLLQQEKELSSSLHQKLCSFQEEMAKEKNLFEEELKQTLDELDKLQQKEEQAERLVK
     ||-|---||-|-||||||-|-|||||||-|-|-||||||-|-|||||-|-||||||--|-|-||||---||||-||-||||
  1  MQILTERLALERQEYEKLQQKELQSQSLLQQEKELSARLQQQLCSFQEEMTSEKNVFKEELKLALAELDAVQQKEEQSERLVK

84  QLEEEAKSRAEELKLLEEKLKGKEAELEKSSAAHTQATLLLQEKYDSMVQSLEDVT..................
     |||||-||-|||-|-|-||-|-|-|||-|-|||-|-||-|||-|-|-||-|-||
 84  QLEEERKSTAEQLTRLDNLLREKEVELEKHIAAHAQAILIAQEKYNDTAQSLRDVTAQLESVQEKYNDTAQLESE

140  ..........................................AQFESYKALTASEIEDLKLENSSLQE
                                                |-|||||-|---|-|||||||||||||
167  QEKYNDTAQSLRDVTAQLESEQEKYNDTAQSLRDVSAQLESYKSSTLKEIEDLKLENLTLQE

166  KVAKAGKNAEDVQHQILATESSNQEYVRMLLDLQTKSALKETEIKEITVSFLQKITDLQNQLKQQEEDFRKQLEDEEGRKAEK
     ||-|-|-|||-||||||||||-|-|||-|-||||-|||-|-||||||||-|-|||||-|-|||-|-|--|||-|-|---|||
250  KVAMAEKSVEDVQQQILTAESTNQEYARMVQDLQNRSTLKEEEIKEITSSFLEKITDLKNQLRQQDEDFRKQLEEKGKRTAEK

249  ENTTAELTEEINKWRLLYEELYNKTKPFQLQLDAFEVEKQALLNEHGAAQEQLNKIRDSYAKLLGHQNLKQKIKHVVKLKDEN
     ||--|-||||||||||||||||-|-||||||||||-|||-||||||||||-|-|||||||||||||||||||||||||||||
333  ENVMTELTMEINKWRLLYEELYEKTKPFQQQLDAFEAEKQALLNEHGATQEQLNKIRDSYAQLLGHQNLKQKIKHVVKLKDEN

332  SQLKSEVSKLRCQLAKKKTK*....................
     |||||||||||-||-|-|-|---
416  SQLKSEVSKLRSQLVKRKQNELRLQGELDKALGIRHFDPSKAFCHASKENFTPLKEGNPNCC*
```

FIGURE 1

METHOD FOR DETECTING THE PRESENCE OF A POLYNUCLEOTIDE ENCODING A HYALURONAN RECEPTOR EXPRESSED IN HUMAN UMBILICAL VEIN ENDOTHELIAL CELLS

This application is a divisional application of U.S. application Ser. No. 08/700,178 filed Aug. 20, 1996, now U.S. Pat. No. 5,783,669, which is a divisional application of U.S. application Ser. No. 08/402,217 filed Mar. 10, 1995, now U.S. Pat. No. 5,587,301.

OVERVIEW

All blood vessels are composed of three layers or tunics. The tunica intima consists of endothelial cells which line the vessel and rest on the basal lamina or middle layer. The subendothelial layer consists of loose connective tissue and may contain smooth muscle cells. The endothelial cells and are generally polygonal and are elongated in the direction of blood flow. The nuclei of the endothelial cells bulge into the capillary lumen, and Golgi complexes are is located at the nuclear poles. A few mitochondria, free ribosomes, and rough endoplasmic reticulum are present. Endothelial cells are held together by zona occludentes and an occasional desmosome; and gap junctions which offer variable permeability to macromolecules are present. The Weibel Palade body, a rod shaped cytoplasmic inclusion, is characteristic of these cells.

Vascular endothelial cells play a central role in physiological homeostasis, blood vessel permeability, and response to physiologic and pathologic stimuli. The endothelium is a primary target for cardiovascular risk factors such as high blood pressure, shear stress, and atherosclerosis. It is sensitive to endothelin, growth factors, interleukin 1, epinephrine, angiotensin, arginine vasopressin, heparin, bradykinin, acetylcholine, and prostacyclin, etc.

Hyaluronan (HA) is a negatively charged, high molecular weight, connective tissue polysaccharide found in the extracellular matrix of most animal tissues. It is synthesized in the plasma membrane of fibroblasts and other cells and is catabolized locally as well as in the lymph nodes or liver sinusoids. HA is commonly isolated from the vitreous body of the eye, synovial fluid, umbilical cord, and skin. It has several physiological functions including roles in water and plasma protein homeostasis; mitosis, cell migration, and differentiation, including angiogenesis (Rooney P and Kumar S (1994) EXS (Switzerland) 70:179–90); and tissue remodeling, as either a normal or a tumor-associated event.

The matrix-induced effects on cells are directed by a wide variety of HA-binding proteins, such as the hyaluronan receptor (HR). The widespread occurrence of HRs indicate their importance in tissue organization and control of cellular behavior. The family is known as the hyaladherins and includes those HA-binding proteins which act as part of the structural matrix and those which interact with HA at the plasma membrane as cell-surface matrix receptors. With the recognition of the hyaluronan cell-surface receptor (HR), cell biologists, pathologists, and immunologists have begun to investigate the importance of the HA and HR for potential diagnostic and therapeutic value.

Matrix Hyaladherins

HRs found within the cartilage matrix have been well characterized. Aggrecan is the large aggregating chondroitin sulfate proteoglycan of cartilage which has a high affinity for HA. Link protein is a 45–48 kDa glycoprotein which also demonstrates strong specific binding affinity. HA may bind more than 100 aggrecan and link protein molecules in a supramolecular complex which confers the viscoelastic properties of cartilage. Other matrix proteins such as PG-M and type VI collagen which participate in assembly and integrity may also be involved.

HA-binding proteins are also found in noncartilaginous tissues. Versican in fibroblasts, hyaluronectin in nervous and soft connective tissues, glial hyaluronan binding protein in the central nervous system, and neurocan, a chondroitin sulfate proteoglycan in the brain, also form strong structural complexes with HA. All matrix hyaloadherins contain tandem repeated B loops, a structural motif believed to contain the HA-binding domain.

HR hyaloadherins have been detected on several cell types from a wide variety of tissues. Some reports suggest that HR, are related to the CD44 family of lymphocyte homing receptors, which includes the isoforms Pgp-1, Hermes antigen, H-CAM, and ECMRIII, etc. The distal extracellular domain of CD44 has sequence homology to one of the B loop motifs of link protein. The numerous isoforms suggest different cellular functions and demonstrate binding to other ligands such as collagens I and IV and mucosal vascular addressin.

Other non-CD44 HRs include cell-surface antigens termed IVd4, which block binding of HA, liver endothelial cell receptors (LEC), which are involved in the clearance of HA from the circulation, and fibroblast-produced HR, which may be located on the cell surface where it mediates HA-induced cell locomotion. Its 58 kDA soluble form contains an HA-binding component unrelated to the B loop motif and is known as receptor for HA mediated motility (RHAMM). The important distinctions between cell-surface and matrix hyaloadherins are that HA hexasaccharides represent the minimum size molecule that interacts with these cell-surface receptors, that binding affinity increases with increasing polymer length, and that binding increases with increasing buffer ionic strength.

Cell Migration

Increased matrix presence of HA has been correlated with cell migration in embryogenesis, limb regeneration, wound healing and tumor invasion. Since the CD44 HRs have been shown to associate with the cytoskeletal ankyrin, proteins of the HR complex may affect reorganization of the actin cytoskeleton and other activities such as cell ruffling, detachment from the substratum, and locomotion necessary for cell migration. RHAMM, as one of the HR complex proteins, binds to HA with high affinity and is expressed only in the leading lamellae and perinuclear regions of migrating fibroblasts. Since RHAMM does not include a transmembrane hydrophobic region, it is assumed to be a peripheral protein associated with intracellular, membrane-bound tyrosine kinase. In studies of timed administration of HA and an inhibitor of tyrosine kinase, HA stimulated locomotion via a rapid tyrosine kinase signal transduction pathway.

Tumor Invasion and Metastasis

Invasive or metastatic cancer cells have the capacity to exit from the vascular system by use of sets of molecules, at least one of which always has a receptor function. One series of such sets might include successive interactions among endothelial VLA-4 integrin and E-selectin, subendothelial collagen IV and β-4 integrin, and soft connective tissue HA and CD44 or HR interactions (Zetter BR (1993) Semin Cancer Biol 4:215–218).

Some tumor cells also have the capacity to assemble HA-enriched pericellular matrices which reduce cell adhesion to the outside of the growing tumor and protect the tumor from immune surveillance. In addition, the presence of high HA attracts endothelial cells which are active in angiogenesis. The combination of these HA functions allows the rapid establishment and growth of invasive tumor cells.

The transforming oncogene H-ras may promote cell locomotion. Hardwick et al (1992 J Cell Biol 117:1350 1350) reported that H-ras actually regulates expression of RHAMM, showed binding between HA and RHAMM, and produced an antibody to the protein which is capable of inhibiting HA/HR locomotion.

SUMMARY OF THE INVENTION

The subject invention provides nucleotide sequences which uniquely encode a novel human hyaluronan receptor. cDNA, known as hr, was fully contained within Incyte Clone No. 39200 and encodes a polypeptide designated HR.

The invention also comprises diagnostic tests which include the step of testing a sample or an extract with hr nucleic acids, fragments, or oligomers thereof. Aspects of the invention include the antisense DNA of hr; cloning or expression vectors containing hr; host cells or organisms transformed with expression vectors containing hr; a method for the production and recovery of purified HR from host cells; and purified protein, HR, which can be used to generate antibodies and other molecules for diagnosis of activated, angiogenic, inflamed, or metastatic cells and/or tissues.

DESCRIPTION OF THE FIGURES

FIG. 1 shows the amino acid (aa) alignment of HR (SEQ ID NO:2) with mouse hyaluronan receptor (SEQ ID NO:3). The unmatched aa in the middle of the sequence may reflect the position of a mouse intron. The cDNA lacks the intron since it was constructed from mRNA. Alignments shown were produced using the multisequence alignment program of DNASTAR software (DNASTAR Inc, Madison Wis.).

DETAILED DESCRIPTION OF THE INVENTION

Definitions

Figure 2:
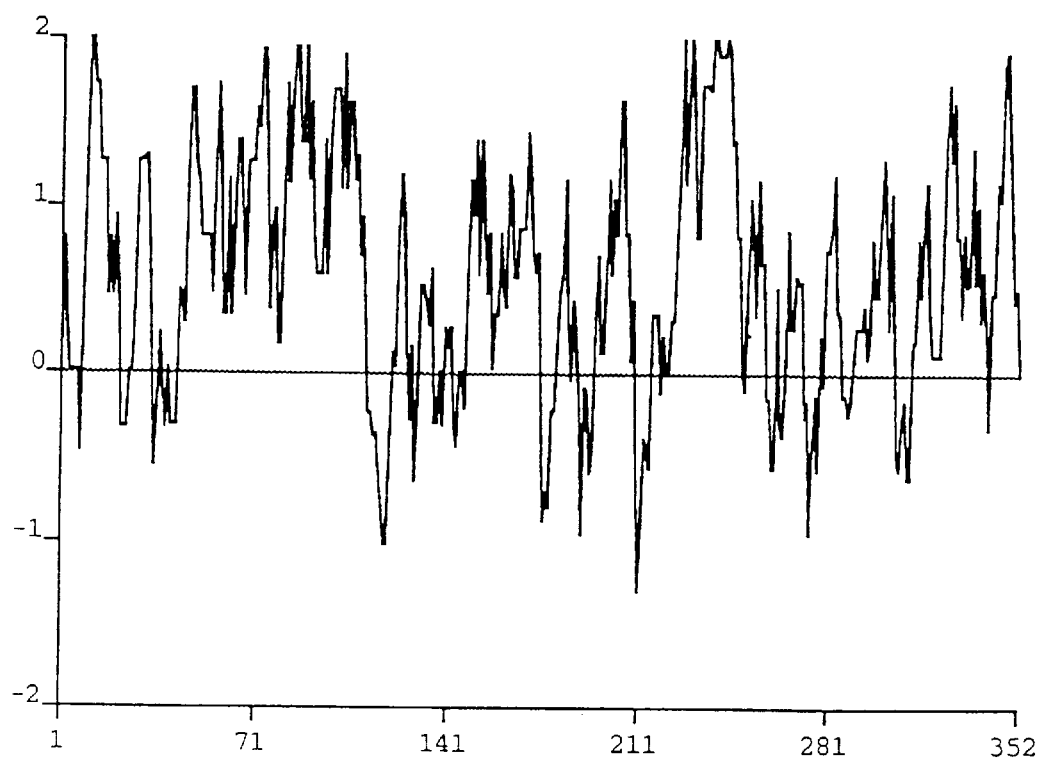
FIG. 2 displays an analysis of HR hydrophobicity based on the predicted aa sequence and composition.

As used herein, HRs, refers to polypeptides, naturally occurring HRs and active fragments thereof, which are encoded by mRNAs transcribed from the cDNA of SEQ ID NO:1.

"Active" refers to those forms of HRs which retain the biologic and/or immunologic activities of any naturally occurring HR.

"Naturally occurring HR" refers to HRs produced by human cells that have not been genetically engineered and specifically contemplates various HRs arising from post-translational modifications of the polypeptide including but not limited to acetylation, carboxylation, glycosylation, phosphorylation, lipidation, and acylation.

"Derivative" refers to HRs chemically modified by such techniques as ubiquitination, labeling (e.g., with radionuclides, various enzymes, etc.), pegylation (derivatization with polyethylene glycol), and insertion or substitution by chemical synthesis of amino acids such as ornithine, which do not normally occur in human proteins.

"Recombinant variant" refers to any polypeptide differing from naturally occurring HRs by amino acid insertions, deletions, and substitutions, created using recombinant DNA techniques. Guidance in determining which amino acid residues may be replaced, added, or deleted without abolishing activities of interest, such as cell adhesion and chemotaxis, may be found by comparing the sequence of the particular HR with that of homologous receptors and minimizing the number of amino acid sequence changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative amino acid replacements. "Insertions" or "deletions" are typically in the range of about 1 to 5 amino acid. The variation allowed may be experimentally determined by systematically making insertions, deletions, or substitutions of amino acid in an HR molecule using recombinant DNA techniques and assaying the resulting recombinant variants for activity.

Where desired, a "signal or leader sequence" can direct the polypeptide through the membrane of a cell. Such a sequence may be naturally present on the polypeptides of the present invention or may be provided from heterologous protein sources by recombinant DNA techniques.

A polypeptide "fragment," "portion," or "segment" is a stretch of amino acid residues of at least about 5 amino acids, often at least about 7 amino acid, typically at least about 9 to 13 amino acid, and, in various embodiments, at least about 17 or more amino acid. To be active, any HR polypeptide must have sufficient length to display biologic and/or immunologic activity.

An "oligonucleotide" or polynucleotide "fragment", "portion," or "segment" is a stretch of nucleotide residues which is long enough for use in polymerase chain reaction (PCR) or in various hybridization procedures to amplify or simply reveal related parts of mRNA or DNA molecules.

The present invention includes purified HR polypeptide from natural or recombinant sources, including cells transformed with recombinant nucleic acid molecules encoding HR. Various methods for the isolation of HR polypeptides may be accomplished by procedures well known in the art. For example, such polypeptides may be purified by immunoaffinity chromatography by employing the antibodies provided by the present invention. Various other methods of protein purification well known in the art include those described in Deutscher M (1990) Methods in Enzymology, Vol 182, Academic Press, San Diego; and Scopes R (1982) Protein Purification: Principles and Practice, Springer-Verlag, New York, NY both incorporated herein by reference.

"Recombinant" may also refer to a polynucleotide which encodes HR and is prepared using recombinant DNA techniques. The DNA which encodes HR may also include allelic or recombinant variants and mutants thereof.

"Oligonucleotides" or "nucleic acid probes" are prepared based on the cDNA sequence which encodes HR provided by the present invention. Oligonucleotides comprise portions of the DNA sequence having at least about 15 nucleotides, usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs encoding HR are present in a cell or tissue or to isolate similar nucleic acid sequences from chromosomal DNA as described by Walsh PS et al (1992 PCR Methods Appl 1:241–250).

Probes may be derived from naturally occurring or recombinant single- or double-stranded nucleic acids or may be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, NY; or Ausubel FM et al (1989) Current Protocols in Molecular Biology, John Wiley & Sons, NYC, both incorporated herein by reference.

"Activated" cells as used in this application are those which are engaged in migration, proliferation, vascularization or differentiation as part of a normal or disease process.

Recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide and change ligand-binding affinities and interchain affinities, or polypeptide degradation or turnover rates.

Detailed Description of the Invention

The present invention provides nucleotide sequences uniquely identifying a novel human hyaluronan receptor, HR, which was highly expressed in the human umbilical vein endothelial library. Because HR is specifically expressed in embryonic tissue, the nucleic acid (hr), polypeptide (HR), and antibodies to HR are useful in diagnostic assays for invasive cancers. Excessive expression of HR can direct cell migration, including lymphocytes and/or other cells which respond to hyaluronan. Therefore, a diagnostic test for excess expression of HR can accelerate diagnosis and proper treatment of an abnormal condition caused by viral or other infections; angiogenesis of cancerous tissues; invasive leukemias and lymphomas; or other physiologic/pathologic problems which deviate from normal development and result in metastatic cell migration, proliferation, vascularization, and differentiation.

Nucleotide sequences encoding HR (or complements thereof) have numerous applications in techniques known to those skilled in the art of molecular biology. These techniques include use as hybridization probes, use as oligomers for PCR, use for chromosome and gene mapping, use in the recombinant production of HR, and use in generation of antisense DNA or RNA and chemical analogs thereof etc. Uses of the nucleotide sequences encoding HR disclosed herein are exemplary of known techniques and are not intended to limit the use of these sequences any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of HR-encoding nucleotide sequences, some bearing minimal homology to the nucleotide sequence of any known and naturally occurring gene, may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring HR, and all such variations are to be considered as being specifically disclosed.

Although nucleotide sequences which encode HR and its variants are preferably capable of hybridizing to the nucleotide sequence of the naturally occurring HR gene under stringent conditions, it may be advantageous to produce nucleotide sequences encoding HR or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding HR and its derivatives without altering the encoded amino acid sequence include the production of RNA transcripts having more desirable properties, such as a greater half-life, than transcripts produced from the naturally occurring sequence.

The nucleotide sequence encoding HR may be joined to a variety of other nucleotide sequences by means of well established recombinant DNA techniques (cf Sambrook J et al. (1989) Molecular Cloning: A Laboratory Manual, Cold Spring Harbor Laboratory, NY). Useful nucleotide sequences for joining to hr include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for hr-specific nucleic acid hybridization probes capable of hybridizing with naturally occurring nucleotide sequences encoding HR. Such probes may also be used for the detection of similar hyaluronan receptor encoding sequences and should preferably contain at least 50% of the nucleotides from this hr encoding sequence. The hybridization probes of the subject invention may be derived from the nucleotide sequence of the SEQ ID NO:1 or from genomic sequence including promoter, enhancer elements, and introns of the respective naturally occurring hrs. Hybridization probes may be labeled by a variety of reporter groups, including radionuclides such as 32P or by 35S, or enzymatic labels such as alkaline phosphatase coupled to the probe via avidin/biotin coupling systems, and the like.

PCR, as described in U.S. Pat. Nos. 4,683,195; 4,800,195; and 4,965,188, provides additional uses for oligonucleotides based upon the nucleotide sequences which encode HR. Such probes used in PCR may be of recombinant origin, chemically synthesized, or a mixture of both, and may comprise a discrete nucleotide sequence for diagnostic use or a degenerate pool of possible sequences for identification of closely related genomic sequences.

Other means of producing specific hybridization probes for hr DNAs include the cloning of nucleic acid sequences encoding HR or HR derivatives into vectors for the production of mRNA probes. Such vectors are known in the art, are commercially available, and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding HR and its derivatives entirely by synthetic chemistry, after which the gene can be inserted into any of the many available DNA vectors using reagents and cells that are known in the art at the time of the filing of this application. Moreover, synthetic chemistry may be used to introduce mutations into the hr sequences or any portion thereof.

The nucleotide sequence can be used to construct an assay to detect inflammation or disease associated with abnormal levels of expression of HR. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of inflammation and/or disease.

The nucleotide sequence for hr can be used to construct hybridization probes for mapping that gene. The nucleotide sequence provided herein may be mapped to a chromosome and specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York, N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of hr on a physical chromosomal map and a specific disease (or predisposition to a specific disease) can help delimit the region of DNA associated with that genetic disease. The nucleotide sequence of the subject invention may be used to detect differences in gene sequence between normal and carrier or affected individuals.

The nucleotide sequence encoding HR may be used to produce purified HR using well known methods of recombinant DNA technology. Among the many publications that teach methods for the expression of genes after they have been isolated is Goeddel (1990) Gene Expression Technology, Methods and Enzymology, Vol 185, Academic Press, San Diego, CA. HR may be expressed in a variety of host cells, either prokaryotic or eukaryotic. Host cells may be from the same species in which hr nucleotide sequences are endogenous or from a different species. Advantages of producing HR by recombinant DNA technology include obtaining adequate amounts of the protein for purification and the availability of simplified purification procedures.

Cells transformed with DNA encoding HR may be cultured under conditions suitable for the expression of hyaluronan receptors and recovery of the protein from the cell culture. HR produced by a recombinant cell may be secreted or may be contained intracellularly, depending on the particular genetic construction used. In general, it is more convenient to prepare recombinant proteins in secreted form. Purification steps vary with the production process and the particular protein produced.

In addition to recombinant production, fragments of HR may be produced by direct peptide synthesis using solid-phase techniques (cf Stewart et al (1969) Solid-Phase Peptide Synthesis, WH Freeman Co, San Francisco; Merrifield J (1963) J Am Chem Soc 85:2149–2154. In vitro protein synthesis may be performed using manual techniques or by automation. Automated synthesis may be achieved, for example, using the Applied Biosystems 431A peptide synthesizer (Foster City, Calif.) in accordance with the instructions provided by the manufacturer. Various fragments of HR may be chemically synthesized separately and combined using chemical methods to produce the full length molecule.

HR for antibody induction does not require biological activity, however, the protein must be immunogenic. Peptides used to induce specific antibodies may have an aa sequence consisting of at least five amino acids, preferably at least 10 amino acid. They should mimic a portion of the aa sequence of the protein and may contain the entire amino acid sequence of a small naturally occurring molecules like HR. Short stretches of HR amino acids may be fused with those of another protein such as keyhole limpet hemocyanin and antibody produced against the chimeric molecule.

Antibodies specific for HR may be produced by inoculation of an appropriate animal with the polypeptide or an antigenic fragment. An antibody is specific for HR if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse WD et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding HR.

An additional embodiment of the subject invention is the use of HR specific antibodies, inhibitors, or analogs as bioactive agents to treat viral or other infections; angiogenesis of cancerous tissues; invasive leukemias and lymphomas; or other physiologic/pathologic problems which deviate from normal development and result in metastatic cell migration, proliferation, vascularization and differentiation.

Bioactive compositions comprising agonists, antagonists, or inhibitors of HR may be administered in a suitable therapeutic dose determined by any of several methodologies including clinical studies on mammalian species to determine maximum tolerable dose and on normal human subjects to determine safe dosage. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating invasive cancers.

The examples below are provided to illustrate the subject invention. These examples are provided by way of illustration and are not included for the purpose of limiting the invention.

EXAMPLES

I Isolation of mRNA and Construction of the cDNA Library

The hyaluronan receptor cDNA sequence was identified among the sequences comprising the HUVEC library. The HUVEC cell line is a normal, homogeneous, well-characterized, early passage, endothelial cell culture from human umbilical vein (Cell Systems Corporation, 12815 NE 124th St, Kirkland, Wash. 98034).

The HUVEC cDNA library was custom constructed by Stratagene (11099 M. Torrey Pines Rd., La Jolla, Calif. 92037). cDNA synthesis was primed with oligo dT hexamers, and synthetic adaptor oligonucleotides were ligated onto the cDNA ends to enable its insertion into the UNI-ZAP vector system (Stratagene). This allowed high efficiency uni-directional (sense orientation) lambda library construction and the convenience of a plasmid system with blue/white color selection to detect clones with cDNA insertions.

The quality of the cDNA library was screened using DNA probes, and then, the pBLUESCRIPT phagemid (Stratagene) was excised. This phagemid allows the use of a plasmid system for easy insert characterization, sequencing, site-directed mutagenesis, the creation of uni-directional deletions and expression of fusion polypeptides. Subsequently, the custom-constructed library phage particles were infected into *E. coli* host strain XL1-BLUE (Stratagene). The high transformation efficiency of this bacterial strain increases the probability that the cDNA library will contain rare, under-represented clones. Alternative unidirectional vectors might include, but are not limited to, pcDNAI (Invitrogen) and pSHIox-1 (Novagen).

II Isolation of cDNA Clones

The phagemid forms of individual cDNA clones were obtained by the in vivo excision process, in which XL1-BLUE was coinfected with an f1 helper phage. Proteins derived from both lambda phage and f1 helper phage initiated new DNA synthesis from defined sequences on the lambda target DNA and create a smaller, single-stranded circular phagemid DNA molecule that includes all DNA sequences of the pBLUESCRIPT plasmid and the cDNA insert. The phagemid DNA was released from the cells and purified, then used to reinfect fresh bacterial host cells (SOLR, Stratagene), where the double-stranded phagemid DNA was produced. Because the phagemid carries the gene for β-lactamase, the newly transformed bacteria were selected on medium containing ampicillin.

Phagemid DNA was purified using the QIAWELL-8 plasmid purification system (QIAGEN Inc, 9259 Eton Ave, Chatsworth, Calif. 91311). This technique provides a rapid and reliable high-throughput method for lysing the bacterial cells and isolating highly purified phagemid DNA. The DNA eluted from the purification resin was suitable for DNA sequencing and other analytical manipulations.

III Sequencing of cDNA Clones

The cDNA inserts from random isolates of the HUVEC library were sequenced in part. Methods for DNA sequencing are well known in the art. Conventional enzymatic methods employed DNA polymerase Kienow fragment, SEQUENASE (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Applied Biosystems 800 and 373 DNA sequencer).

IV Homology Searching of cDNA Clones and Deduced Proteins

Each sequence so obtained was compared to sequences in GenBank using a search algorithm developed by Applied Biosystems Inc. and incorporated into the INHERIT 670 Sequence Analysis System. In this algorithm, Pattern Specification Language (developed by TRW Inc.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

V Identification, Full Length Sequencing and Translation of the Gene INHERIT 670 analysis of the randomly picked and sequenced portions of clones from the HUVEC library identified the partial sequence from Incyte 39200 as homologous to hyaluronan receptor from mouse (Hardwick et al (1992) J Cell Biol 117:1343 1350). The cDNA insert comprising Incyte 39200 was fully sequenced using the same methods described above. The coding region of the insert (ATG-→TGA) was identified and is shown as SEQ ID NO:1. This sequence for human hr was translated using DNASTAR software, the in-frame translation was identified, and is shown in SEQ ID NO:2. When all three possible predicted translations of the sequence were searched against protein databases such as SwissProt and PIR, no exact matches were found to the possible translations of hr. FIG. 1 shows the degree of amino acid homology between HR and mouse RHAMM. The unmatched amino acid in the middle of the sequence may reflect the position of a mouse intron. The cDNA lacks the intron since it was constructed from mRNA. FIG. 2 shows the hydrophobicity plot for HR.

VI Antisense analysis

Knowledge of the correct, complete cDNA sequence of HR will enable its use in antisense technology in the investigation of gene function. Either oligonucleotides, genomic or cDNA fragments comprising the antisense strand of hr can be used either in vitro or in vivo to inhibit expression of the mRNA. Such technology is now well known in the art, and probes can be designed at various locations along the nucleotide sequences. By treatment of cells or whole test animals with such antisense sequences, the gene of interest can be effectively turned off. Frequently, the function of the gene can be ascertained by observing behavior at the cellular, tissue or organismal level (e.g. lethality, loss of differentiated function, changes in morphology, etc.).

In addition to using sequences constructed to interrupt transcription of the open reading frame, modifications of gene expression can be obtained by designing antisense sequences to intron regions, promoter/enhancer elements, or even to trans-acting regulatory genes. Similarly, inhibition can be achieved using Hogeboom base-pairing methodology, also known as "triple helix" base pairing.

VII Expression of HR

Expression of hr may be accomplished by subcloning the cDNAs into appropriate expression vectors and transfecting the vectors into an appropriate expression hosts. In this particular case, the cloning vector previously used for the generation of the tissue library also provides for direct expression of hr sequences in E. coli. Upstream of the cloning site, this vector contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or oligonucleotide linker inclusion.

The hr cDNA can be shuttled into other vectors known to be useful for expression of protein in specific hosts. Oligonucleotide amplimers containing cloning sites as well as a segment of DNA sufficient to hybridize to stretches at both ends of the target cDNA (25 bases) can be synthesized chemically by standard methods. These primers can then used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow selection in bacteria. In addition, the vectors may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced HR can be recovered from the conditioned medium and analyzed using chromatographic methods known in the art.

VIII Isolation of Recombinant HR

HR may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen, San Diego, Calif.) between the purification domain and the hr sequence may be useful to facilitate expression of HR.

IX Production of HR Specific Antibodies

Two approaches are utilized to raise antibodies to HR, and each approach is useful for generating either polyclonal or monoclonal antibodies. In one approach, denatured protein from the reverse phase HPLC separation is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of HR, as deduced from translation of the cDNA, is analyzed to determine regions of high immunogenicity. Oligopeptides comprising appropriate hydrophilic regions, as illustrated in FIG. 2, are synthesized and used in suitable immunization protocols to raise antibodies. Analysis to select appropriate epitopes is described by Ausubel FM et al (1989, Current Protocols in Molecular Biology, John Wiley & Sons, New Yorkm, NY). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems 431A peptide synthesizer Model using fmoc-chemistry and coupled to keyhole limpet hemocyanin (KLH, Sigma) by reaction with M-maleimidobenzoyl-N-hydroxysuccinimide ester (MBS; cf. Ausubel FM et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas may also be prepared and screened using standard techniques. Hybridomas of interest are detected by screening with labeled HR to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled HR at 1 mg/ml. Clones producing antibodies will bind a quantity of labeled HR which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least 10e8 Me-1, preferably 10e9 to 10e10 or stronger, will typically be made by standard procedures as described in Harlow and Lane (1988) Antibodies: A Laboratory Manual. Cold Spring Harbor Laboratory NY; and in Goding (1986) Monoclonal Antibodies: Principles and Practice, Academic Press, New York, N.Y. both incorporated herein by reference.

X Diagnostic Test Using HR Specific Antibodies

Particular HR antibodies are useful for the diagnosis of prepathologic conditions, and chronic or acute diseases which are characterized by differences in the amount or distribution of HR, respectively. To date, HR has only been found in the HUVEC library and is thus specific for abnormalities or pathologies which affect embryonic, angiogenic or invasive cells.

Diagnostic tests for HR include methods utilizing the antibody and a label to detect HR in human body fluids, tissues or extracts of such tissues. The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. No. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound HR, using either polyclonal or monoclonal antibodies specific for the protein, are known in the art. Examples include enzyme-linked immunosorbent assay (ELISA), radioimmunoass.ay (RIA) and fluorescent activated cell sorting (FACS). A two-site monoclonal-based immunoassay utilizing monoclonal antibodies reactive to two non-interfering epitopes on HR is preferred, but a competitive binding assay may be employed. These assays are described, among other places, in Maddox, Del. et al (1983, J Exp Med 158:1211).

XI Purification of Native HR Using Specific Antibodies

Native or recombinant HR can be purified by immunoaffinity chromatography using antibodies specific for HR. In general, an immunoaffinity column is constructed by covalently coupling the anti-HR antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE (Pharmacia LKB Biotechnology). The antibody is coupled to the resin, the resin is blocked, and the derivative resin is washed according to the manufacturer's instructions.

Such immunoaffinity columns were utilized in the purification of HR by preparing a fraction from cells containing HR in a soluble form. This preparation was derived by solubilization of the whole cell or of a subcellular fraction obtained via differential centrifugation by the addition of detergent or by other methods well known in the art. Alternatively, soluble HR containing a signal sequence may be secreted in useful quantity into the medium in which the cells are grown.

A soluble HR-containing preparation was passed over the immunoaffinity column, and the column was washed under conditions that allow the preferential absorbance of HR (eg, high ionic strength buffers in the presence of detergent). Then, the column was eluted under conditions that disrupt antibodylHR binding (e.g., a buffer of pH 2–3 or a high concentration of a chaotrope such as urea or thiocyanate ion), and HR was collected.

XII Hyaluronan Induced Chemotaxis for Cell Activation and Wound Healing

The chemotactic interactions between HA and HR were measured in a 48-well microchemotaxis chambers (cf. Falk WR et al (1980) J Immunol Methods 33:239). In each well, two compartments are separated by a filter that allows the passage of cells in response to a chemical gradient. Cells expressing HR in a culture medium such as RPMI 1640 (Sigma, St. Louis Mo.) are placed on one side of a filter, usually polycarbonate, and cells producing HA or a solution enriched with HA are placed on the opposite side of the filter. Sufficient incubation time is allowed for the cells to traverse the filter in response to the concentration gradient across the filter. Filters are recovered from each well, and cells adhering to the side of the filter facing the HA are typed and quantified.

Those cells producing HR and migrating toward the higher end of the HA gradient are rated for chemotactic specificity. This assay not only substantiates the ability of HR-producing cells to respond to HA, but provides researchers using methods well known in the art with model systems from which to obtain and describe transcription factors and enhancers specific for use in regulating HR activity in native cell populations. The ability to artificially supply such factors dissolved in dimethyl sulfoxide (DMSO) or some other carrier liquid, to upregulate production of HR in a localized manner, and to enhance migration capability provides for the use of HA as a stimulant in wound healing. HA could be incorporated in collagenous or other natural or artificial bandage materials used to treat refractory wounds. The presence of HA would attract activated endothelial cells, fibroblasts, etc. which would participate in the repair and healing process.

XIII Drug Screening

This invention is particularly useful for screening compounds by using HR or binding fragments thereof in any of a variety of drug screening techniques. The polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between HR and the agent being tested. Alternatively, one can examine the diminution in complex formation between HR and hyaluronan caused by the agent being tested.

Thus, the present invention provides methods of screening for drugs or any other agents which can affect cell migration, angiogenesis or infiltration of lymphomas or leukemias. These methods comprise contacting such an agent with HR polypeptide or a fragment thereof and assaying (i) for the presence of a complex between the agent and the HR polypeptide or fragment, or (ii) for the presence of a complex between the HR polypeptide or fragment and the cell, by methods well known in the art. In such competitive binding assays, the HR polypeptide or fragment is typically labeled. After suitable incubation, free HR polypeptide or fragment is separated from that present in bound form, and the amount of free or uncomplexed label is a measure of the ability of the particular agent to bind to HR or to interfere with the HR and agent complex.

Another technique for drug screening provides high throughput screening for compounds having suitable binding affinity to the HR polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with HR polypeptide and washed. Bound HR polypeptide is then detected by methods well known in the art. Purified HR can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding HR specifically compete with a test compound for binding to HR polypeptides or fragments thereof. In this manner, the antibodies can be used to detect the presence of any peptide which shares one or more antigenic determinants with HR.

XIV Rational Drug Design

The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (cf Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design efficient inhibitors. Useful examples of rational drug design may include molecules which have improved activity or stability as shown by Braxton S and Wells JA (1992 Biochemistry 31:7796–7801) or which act as inhibitors, agonists, or antagonists of native peptides as shown by Athauda SB et al (1993 J Biochem 113:742–746), incorporated herein by reference.

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amount of polypeptide may be made available to perform such analytical studies as X-ray crystallography. In addition, knowledge of the HR amino acid sequence provided herein will provide guidance to those employing computer modeling techniques in place of or in addition to x-ray crystallography.

XV Identification of Other Members of the HR Complex

Purified HR is useful for characterization and purification of associated cell surface receptors and binding molecules. Cells which respond to HA by chemotaxis or other specific responses are likely to express a receptor for HR and to interact with transmembrane signaling molecules such as tyrosine kinase. Radioactive labels may be incorporated into HR by various methods known in the art. A preferred embodiment is the labeling of primary amino groups in HR with $^{125}$I Bolton-Hunter reagent (Bolton, AE and Hunter, WM (1973) Biochem J 133: 529), which has been used to label other signaling molecules without concomitant loss of biological activity (Hebert CA et al (1991) J Biol Chem 266: 18989; McColl S et al (1993) J Immunol 150:4550–4555). Receptor-bearing cells are incubated with the labeled signaling molecules. The cells are then washed to removed unbound molecules, and receptor-bound labeled molecule is quantified. The data obtained using different concentrations of HR is used to calculate values for the number, affinity, and association of other members of the receptor complex.

Labeled HR is also useful as a reagent for purification of the particular molecule(s) of this complex with which it interacts. In one embodiment of affinity purification, HR is covalently coupled to a chromatography column. Cells and their membranes are extracted, HA is removed and various HA-free subcomponents are passed over the column. HR-associated molecules bind to the column by virtue of their biological affinity. The HR-complex is recovered from the column, dissociated and the recovered molecule is subjected to N-terminal protein sequencing. This amino acid sequence is then used to identify the molecule or to design degenerate oligonucleotide probes for cloning the gene from an appropriate cDNA library.

In an alternate method, mRNA is obtained from HR-complex-bearing cells and made into a cDNA library. The library is transfected into a population of cells, and cells expressing the associated molecule(s) are selected using fluorescently labeled HR. The molecule is identified by recovering and sequencing the recombinant DNA from the highly labeled cells.

In another alternate method, antibodies are raised against HR, specifically monoclonal antibodies. The monoclonal antibodies are screened to identify those which inhibit the binding of labeled HR. These monoclonal antibodies are then used in affinity purification or expression cloning of the associated signaling molecule.

Other soluble binding molecules are identified in a similar manner. Labeled HR is incubated with extracts or other appropriate materials derived from HUVEC cells. After incubation, HR complexes (which are larger than the size of purified HR molecule) are identified by a sizing technique such as size exclusion chromatography or density gradient centrifugation and are purified by methods known in the art.

The soluble binding protein(s) is subjected to N-terminal sequencing to obtain information sufficient for database identification, if the soluble protein is known, or for cloning, if the soluble protein is unknown.

XVI Use and Administration of HR

Antibodies, inhibitors, or antagonists of HR (or other treatments for excessive HR production, hereinafter abbreviated TEHR), can provide different effects when administered therapeutically. TEHRs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TEHR include solubility of the molecule, half-life and antigenicity/immunogenicity; these and other characteristics may aid in defining an effective carrier. Native human proteins are preferred as TEHRs, but organic or synthetic molecules resulting from drug screens may be equally effective in particular situations.

TEHRs may be delivered by known routes of administration including but not limited to topical creams and gels; transmucosal spray and aerosol, transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TEHR to be administered, and the pharmacokinetic profile of the particular TEHR Additional factors which may be taken into account include disease state (e.g. severity) of the patient, age, weight, gender, diet, time of administration, drug combination, reaction sensitivities, and tolerance/response to therapy. Long acting TEHR formulations might be administered every 3 to 4 days, every week, or once every two weeks depending on half-life and clearance rate of the particular TEHR.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TEHRs and that administration targeting metastatic cancers may necessitate delivery in a manner different from that being delivered to vascular endothelial cells.

It is contemplated that conditions or diseases which activate leukocytes may precipitate damage that is treatable with TEHRs. These conditions or diseases may be specifically diagnosed by the tests discussed above, and such testing should be performed in suspected cases of viral or other infections; angiogenesis of cancerous tissues; invasive leukemias and lymphomas; or other physiologic/pathologic problems which deviate from normal development and result in metastatic cell migration, proliferation and differentiation.

All publications and patents mentioned in the above specification are herein incorporated by reference. The foregoing written specification is considered to be sufficient to enable one skilled in the art to practice the invention. Indeed, various modifications of the above described modes for carrying put the invention which are obvious to those skilled in the field of molecular biology or related fields are intended to be within the scope of the following claims.

We claim:

1. A method for detecting the presence of a polynucleotide comprising SEQ ID NO:1 in a sample containing nucleic acids, the method comprising the steps of:

(a) contacting the nucleic acid of the sample with a polynucleotide having a sequence complementary to SEQ ID NO:1 under conditions suitable for formation of a double-stranded nucleic acid complex; and (b) detecting the presence of the complex, wherein the presence of the complex correlates with the presence of the polynucleotide comprising SEQ ID NO:1 in the sample.

2. The method of claim 1, further comprising the steps of:

(a) analyzing the sample to determine the amount of complex present; and (b) comparing the amount of complex present to a standard value, whereby, if the amount of hybridization complex is larger than the standard value, the presence of inflammation or disease is indicated.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1056 base pairs
      (B) TYPE: nucleic acid
      (C) STRANDEDNESS: single
      (D) TOPOLOGY: linear (xi) SEQUENCE DESCRIPTION: SEQ ID NO:1:

```
ATGCAAAACT TAAAACAGAA GTTTATTCTT GAACAACAGG AACGTGAAAA GCTTCAACAA      60

AAAGAATTAC AAATTGATTC ACTTCTGCAA CAAGAGAAAG AATTATCTTC GAGTCTTCAT     120

CAGAAGCTCT GTTCTTTTCA AGAGGAAATG GCTAAAGAGA AGAATCTGTT TGAGGAAGAA     180

TTAAAGCAAA CACTGGATGA GCTTGATAAA TTACAGCAAA AGGAGGAACA AGCTGAAAGG     240

CTGGTCAAGC AATTGGAAGA GGAAGCAAAA TCTAGAGCTG AAGAATTAAA ACTCCTAGAA     300

GAAAAGCTGA AAGGGAAGGA GGCTGAACTG GAGAAAAGTA GTGCTGCTCA TACCCAGGCC     360

ACCCTGCTTT TGGAGGAAAA GTATGACAGT ATGGTGCAAA GCCTTGAAGA TGTTACTGCT     420

CAATTTGAAA GCTATAAAGC GTTAACAGCC AGTGAGATAG AAGATCTTAA GCTGGAGAAC     480

TCATCATTAC AGGAAAAAGT GGCCAAGGCT GGGAAAAATG CAGAGGATGT TCAGCATCAG     540
```

```
ATTTTGGCAA CTGAGAGCTC AAATCAAGAA TATGTAAGGA TGCTTCTAGA TCTGCAGACC       600

AAGTCAGCAC TAAAGGAAAC AGAAATTAAA GAAATCACAG TTTCTTTTCT TCAAAAAATA       660

ACTGATTTGC AGAACCAACT CAAGCAACAG GAGGAAGACT TTAGAAAACA GCTGGAAGAT       720

GAAGAAGGAA GAAAAGCTGA AAAGAAAAT ACAACAGCAG AATTAACTGA AGAAATTAAC        780

AAGTGGCGTC TCCTCTATGA AGAACTATAT AATAAAACAA AACCTTTTCA GCTACAACTA       840

GATGCTTTTG AAGTAGAAAA ACAGGCATTG TTGAATGAAC ATGGTGCAGC TCAGGAACAG       900

CTAAATAAAA TAAGAGATTC ATATGCTAAA TTATTGGGTC ATCAGAATTT GAAACAAAAA       960

ATCAAGCATG TTGTGAAGTT GAAAGATGAA AATAGCCAAC TCAAATCGGA AGTATCAAAA      1020

CTCCGCTGTC AGCTTGCTAA AAAAAAAACA AAGTGA                                1056

(2) INFORMATION FOR SEQ ID NO:2:

(i) SEQUENCE CHARACTERISTICS:
        (A) LENGTH: 351 amino acids
        (B) TYPE: amino acid
        (C) STRANDEDNESS: single
        (D) TOPOLOGY: linear (xi) SEQUENCE DESCRIPTION: SEQ ID NO:2:

Met Gln Asn Leu Lys Gln Lys Phe Ile Leu Glu Gln Gln Glu Arg Glu
1               5                   10                  15

Lys Leu Gln Gln Lys Glu Leu Gln Ile Asp Ser Leu Leu Gln Gln Glu
            20                  25                  30

Lys Glu Leu Ser Ser Ser Leu His Gln Lys Leu Cys Ser Phe Gln Glu
        35                  40                  45

Glu Met Ala Lys Glu Lys Asn Leu Phe Glu Glu Leu Lys Gln Thr
    50                  55                  60

Leu Asp Glu Leu Asp Lys Leu Gln Gln Lys Glu Gln Ala Glu Arg
65                  70                  75                  80

Leu Val Lys Gln Leu Glu Glu Glu Ala Lys Ser Arg Ala Glu Glu Leu
            85                  90                  95

Lys Leu Leu Glu Glu Lys Leu Lys Gly Lys Glu Ala Glu Leu Glu Lys
            100                 105                 110

Ser Ser Ala Ala His Thr Gln Ala Thr Leu Leu Glu Glu Lys Tyr
        115                 120                 125

Asp Ser Met Val Gln Ser Leu Glu Asp Val Thr Ala Gln Phe Glu Ser
130                 135                 140

Tyr Lys Ala Leu Thr Ala Ser Glu Ile Glu Asp Leu Lys Leu Glu Asn
145                 150                 155                 160

Ser Ser Leu Gln Glu Lys Val Ala Lys Ala Gly Lys Asn Ala Glu Asp
            165                 170                 175

Val Gln His Gln Ile Leu Ala Thr Glu Ser Ser Asn Gln Glu Tyr Val
        180                 185                 190

Arg Met Leu Leu Asp Leu Gln Thr Lys Ser Ala Leu Lys Glu Thr Glu
    195                 200                 205

Ile Lys Glu Ile Thr Val Ser Phe Leu Gln Lys Ile Thr Asp Leu Gln
    210                 215                 220

Asn Gln Leu Lys Gln Gln Glu Glu Asp Phe Arg Lys Gln Leu Glu Asp
225                 230                 235                 240

Glu Glu Gly Arg Lys Ala Glu Lys Glu Asn Thr Thr Ala Glu Leu Thr
            245                 250                 255

Glu Glu Ile Asn Lys Trp Arg Leu Leu Tyr Glu Glu Leu Tyr Asn Lys
```

```
                    260                 265                 270
Thr Lys Pro Phe Gln Leu Gln Leu Asp Ala Phe Glu Val Glu Lys Gln
            275                 280                 285

Ala Leu Leu Asn Glu His Gly Ala Ala Gln Glu Gln Leu Asn Lys Ile
        290                 295                 300

Arg Asp Ser Tyr Ala Lys Leu Leu Gly His Gln Asn Leu Lys Gln Lys
305                 310                 315                 320

Ile Lys His Val Val Lys Leu Lys Asp Glu Asn Ser Gln Leu Lys Ser
                325                 330                 335

Glu Val Ser Lys Leu Arg Cys Gln Leu Ala Lys Lys Lys Thr Lys
                340                 345                 350

(2) INFORMATION FOR SEQ ID NO:3:

(i) SEQUENCE CHARACTERISTICS:
        (A) LENGTH: 477 amino acids
        (B) TYPE: amino acid
        (C) STRANDEDNESS: single
        (D) TOPOLOGY: linear (xi) SEQUENCE DESCRIPTION: SEQ ID NO:3:

Met Gln Ile Leu Thr Glu Arg Leu Ala Leu Glu Arg Gln Glu Tyr Glu
1               5                   10                  15

Lys Leu Gln Gln Lys Glu Leu Gln Ser Gln Ser Leu Leu Gln Gln Glu
                20                  25                  30

Lys Glu Leu Ser Ala Arg Leu Gln Gln Gln Leu Cys Ser Phe Gln Glu
            35                  40                  45

Glu Met Thr Ser Glu Lys Asn Val Phe Lys Glu Glu Leu Lys Leu Ala
        50                  55                  60

Leu Ala Glu Leu Asp Ala Val Gln Gln Lys Glu Glu Gln Ser Glu Arg
65                  70                  75                  80

Leu Val Lys Gln Leu Glu Glu Glu Arg Lys Ser Thr Ala Glu Gln Leu
                85                  90                  95

Thr Arg Leu Asp Asn Leu Leu Arg Glu Lys Glu Val Glu Leu Glu Lys
            100                 105                 110

His Ile Ala Ala His Ala Gln Ala Ile Leu Ile Ala Gln Glu Lys Tyr
        115                 120                 125

Asn Asp Thr Ala Gln Ser Leu Arg Asp Val Thr Ala Gln Leu Glu Ser
    130                 135                 140

Val Gln Glu Lys Tyr Asn Asp Thr Ala Gln Ser Leu Arg Asp Val Thr
145                 150                 155                 160

Ala Gln Leu Glu Ser Glu Gln Glu Lys Tyr Asn Asp Thr Ala Gln Ser
                165                 170                 175

Leu Arg Asp Val Thr Ala Gln Leu Glu Ser Glu Gln Glu Lys Tyr Asn
            180                 185                 190

Asp Thr Ala Gln Ser Leu Arg Asp Val Thr Ala Gln Leu Glu Ser Val
        195                 200                 205

Gln Glu Lys Tyr Asn Asp Thr Ala Gln Ser Leu Arg Asp Val Ser Ala
    210                 215                 220

Gln Leu Glu Ser Tyr Lys Ser Ser Thr Leu Lys Glu Ile Glu Asp Leu
225                 230                 235                 240

Lys Leu Glu Asn Leu Thr Leu Gln Gly Lys Val Ala Met Ala Glu Lys
                245                 250                 255

Ser Val Glu Asp Val Gln Gln Ile Leu Thr Ala Glu Ser Thr Asn
            260                 265                 270
```

```
Gln Glu Tyr Ala Arg Met Val Gln Asp Leu Gln Asn Arg Ser Thr Leu
        275                 280                 285

Lys Glu Glu Glu Ile Lys Glu Ile Thr Ser Ser Phe Leu Glu Lys Ile
        290                 295                 300

Thr Asp Leu Lys Asn Gln Leu Arg Gln Gln Asp Glu Asp Phe Arg Lys
305                 310                 315                 320

Gln Leu Glu Glu Lys Gly Lys Arg Thr Ala Glu Lys Glu Asn Val Met
                325                 330                 335

Thr Glu Leu Thr Met Glu Ile Asn Lys Trp Arg Leu Leu Tyr Glu Glu
                340                 345                 350

Leu Tyr Glu Lys Thr Lys Pro Phe Gln Gln Gln Leu Asp Ala Phe Glu
        355                 360                 365

Ala Glu Lys Gln Ala Leu Leu Asn Glu His Gly Ala Thr Gln Glu Gln
        370                 375                 380

Leu Asn Lys Ile Arg Asp Ser Tyr Ala Gln Leu Leu Gly His Gln Asn
385                 390                 395                 400

Leu Lys Gln Lys Ile Lys His Val Val Lys Leu Lys Asp Glu Asn Ser
                405                 410                 415

Gln Leu Lys Ser Glu Val Ser Lys Leu Arg Ser Gln Leu Val Lys Arg
                420                 425                 430

Lys Gln Asn Glu Leu Arg Leu Gln Gly Glu Leu Asp Lys Ala Leu Gly
        435                 440                 445

Ile Arg His Phe Asp Pro Ser Lys Ala Phe Cys His Ala Ser Lys Glu
    450                 455                 460

Asn Phe Thr Pro Leu Lys Glu Gly Asn Pro Asn Cys Cys
465                 470                 475
```